United States Patent
Sugiyama et al.

(10) Patent No.: US 9,435,734 B2
(45) Date of Patent: Sep. 6, 2016

(54) METHOD FOR OBSERVING STEM CELLS, METHOD FOR REMOVAL OF CELL REGION IN STATE TENDING TOWARD DIFFERENTIATION, AND DEVICE FOR OBSERVING STEM CELLS

(71) Applicant: HAMAMATSU PHOTONICS K.K., Hamamatsu-shi, Shizuoka (JP)

(72) Inventors: Norikazu Sugiyama, Hamamatsu (JP); Takuji Kataoka, Hamamatsu (JP); Ikuo Arata, Hamamatsu (JP)

(73) Assignee: HAMAMATSU PHOTONICS K.K., Hamamatsu-shi, Shizuoka (JP)

( * ) Notice: Subject to any disclaimer, the term of this patent is extended or adjusted under 35 U.S.C. 154(b) by 0 days.

(21) Appl. No.: 14/806,999

(22) Filed: Jul. 23, 2015

(65) Prior Publication Data
US 2015/0323454 A1 Nov. 12, 2015

Related U.S. Application Data

(63) Continuation of application No. 14/356,487, filed as application No. PCT/JP2012/077365 on Oct. 23, 2012, now Pat. No. 9,134,296.

(30) Foreign Application Priority Data

Nov. 8, 2011 (JP) .................................. 2011-244867

(51) Int. Cl.
*G01N 21/01* (2006.01)
*G01N 21/47* (2006.01)
(Continued)

(52) U.S. Cl.
CPC .............. *G01N 21/47* (2013.01); *G01N 21/49* (2013.01); *G01N 21/59* (2013.01);
(Continued)

(58) Field of Classification Search
CPC .................. G01N 33/56966; G01N 15/1434; G01N 2021/6439; G01N 2800/52; G01N 33/5005; G01N 33/57407; G01N 33/57492; G01N 15/14; G01N 15/147; G01N 2015/0065; G01N 2015/1006; G01N 2015/1477; G01N 21/6428
See application file for complete search history.

(56) References Cited

U.S. PATENT DOCUMENTS

| 5,260,764 A | 11/1993 | Fukuda et al. |
| 7,564,546 B2 * | 7/2009 | Maier ................... G01J 3/2803 356/301 |

(Continued)

FOREIGN PATENT DOCUMENTS

| EP | 1 696 024 | 8/2006 |
| JP | 2001-286285 A | 10/2001 |

(Continued)

OTHER PUBLICATIONS

RIKEN Center for Developmental Biology Division of Human Stem Cell Technology, "Practical Protocol for Human Pluripotent Stem Cell Culture," 2010, pp. 1-21, including partial English translation.

(Continued)

*Primary Examiner* — Michael P Stafira
(74) *Attorney, Agent, or Firm* — Drinker Biddle & Reath LLP

(57) ABSTRACT

A method for observing stem cells by an observation device 1 comprises, placing stem cells C in a petri dish 11, mounting the petri dish 11 on a waveguide 21 via water 13, emitting illumination light L1 into the waveguide 21 and emitting the illumination light L1 to the stem cells C in the petri dish 11 via the water 13, and detecting scattered light L2, the scattered light L2 being the illumination light L1 emitted to the stem cells C that is scattered by the stem cells C and has passed through the waveguide 21. Then, in the light image detected by means of the scattered light L2, a region that is markedly darker than other regions is identified as being in the state tending toward differentiation.

14 Claims, 16 Drawing Sheets

(51) Int. Cl.
*G01N 33/483* (2006.01)
*G02B 21/08* (2006.01)
*G01N 21/49* (2006.01)
*G01N 33/50* (2006.01)
*G01N 21/59* (2006.01)
*G02B 21/36* (2006.01)

(52) U.S. Cl.
CPC ..... G01N 33/4833 (2013.01); G01N 33/5005 (2013.01); G02B 21/088 (2013.01); *G01N 2201/0446* (2013.01); *G01N 2201/062* (2013.01); *G02B 21/36* (2013.01)

(56) References Cited

U.S. PATENT DOCUMENTS

| 2008/0095669 | A1 | 4/2008 | Kang et al. | |
|---|---|---|---|---|
| 2009/0073456 | A1* | 3/2009 | Wax | G01N 21/4795 356/479 |
| 2010/0062442 | A1* | 3/2010 | Burke | G01N 33/56966 435/6.14 |
| 2011/0092762 | A1* | 4/2011 | Wong | C12N 5/0604 600/34 |
| 2011/0261164 | A1* | 10/2011 | Olesen | G01N 15/1475 348/46 |
| 2013/0027539 | A1* | 1/2013 | Kiyota | C12M 41/36 348/79 |

FOREIGN PATENT DOCUMENTS

| JP | 2004-101196 A | 4/2004 |
|---|---|---|
| JP | 2007-306891 A | 11/2007 |
| WO | WO-2008/153056 A1 | 12/2008 |
| WO | WO-2009/157385 A1 | 12/2009 |

OTHER PUBLICATIONS

English-language translation of International Preliminary Report on Patentability (IPRP) dated May 22, 2014 that issued in WO Patent Application No. PCT/JP2012/077365.

* cited by examiner

Fig. 10
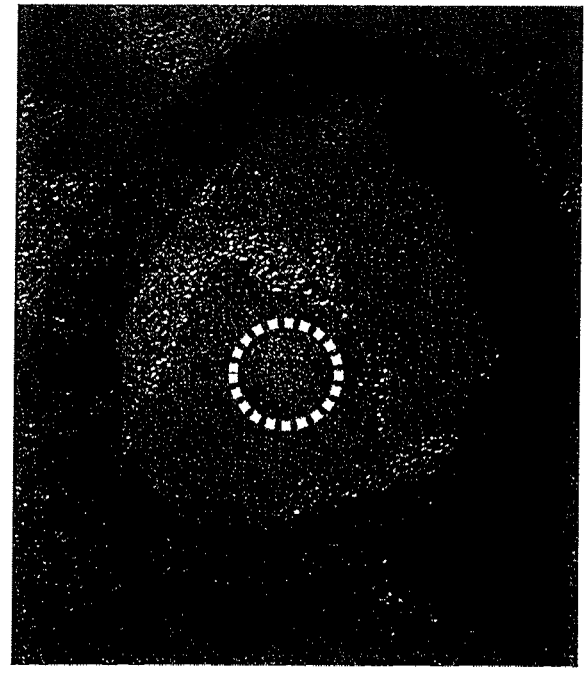
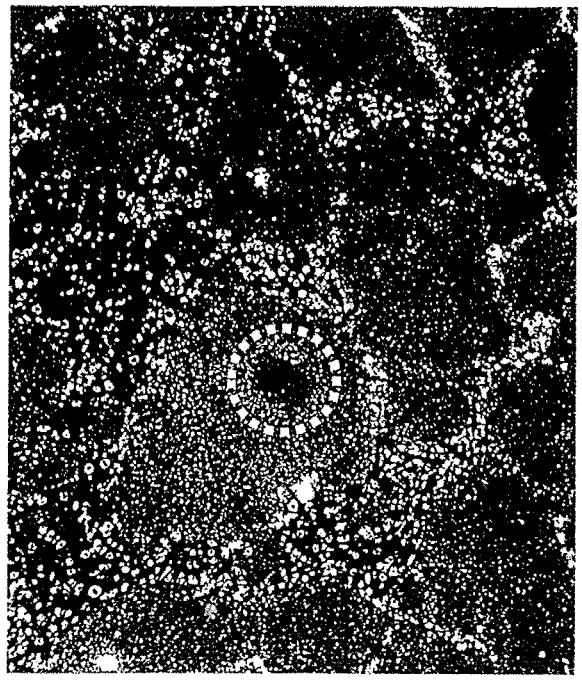

METHOD FOR OBSERVING STEM CELLS, METHOD FOR REMOVAL OF CELL REGION IN STATE TENDING TOWARD DIFFERENTIATION, AND DEVICE FOR OBSERVING STEM CELLS

This is a continuation application of copending application Ser. No. 14/356,487, having a §371 date of May 6, 2014, which is a national stage filing based on PCT International Application No. PCT/JP2012/077365, filed on Oct. 23, 2012. The copending application Ser. No. 14/356,487, which is now U.S. Pat. No. 9,134,296, is incorporated by reference herein in its entirety.

TECHNICAL FIELD

The present invention relates to a method for observing stem cells, a method for removal of a cell region in the state tending toward differentiation, and a device for observing stem cells. Particularly, the present invention relates to a method for observing stem cells that can distinguish between the undifferentiated state and the state tending toward differentiation of stem cells, a method for removal of a cell region identified as being in the state tending toward differentiation, and a device for observing stem cells.

BACKGROUND ART

Stem cells such as embryonic stem cells (ES cells) and induced pluripotent stem cells (iPS cells) derived from humans have an ability to differentiate into a wide variety of cell types. By mass culturing and then differentiating these stem cells into the cells of interest, they can be applied to conventionally difficult large-scale drug efficacy evaluation or medical practice using human cells such as elucidation of disease, drug discovery screening, toxicity test, or regenerative medicine, and in light of this, stem cells are attracting attention.

It is to be noted that, in the process of culturing stem cells while keeping them in the undifferentiated state, some cells fail in maintaining the undifferentiated state and go into the state tending toward differentiation, and from time to time the emergence of such cells led to a deterioration of the quality of the whole stem cells. In light of this, the importance of quality control of stem cells is pointed out; however, in order to exercise proper quality control, it is necessary to monitor stem cells, determine whether the cells are in the differentiated or undifferentiated state, and remove the cells in the state tending toward differentiation, which no longer maintain the undifferentiated state.

As a method for determining whether the cells are in the differentiated or undifferentiated state as mentioned above, conventionally, using an optical microscope such as a phase contrast microscope, a stem cell colony in the undifferentiated state is distinguished from a stem cell colony in the state tending toward differentiation by visually determining transmitted light images obtained by transillumination (for example, see page 17 of Non Patent Literature 1). Then, the colony that is determined to be in the state tending toward differentiation by visual determination is eventually collected and then removed by aspiration using a pipette, etc.

CITATION LIST

Non Patent Literature

Non Patent Literature 1: "A Protocol For Human Pluripotent Stem Cell Culture Practice", [online], RIKEN Center for Developmental Biology, Division of Human Stem Cell Technology, [searched on Sep. 22, 2011], internet address <URL:http://www.cdb.riken.jp/hsct/protocol.html>

SUMMARY OF INVENTION

Technical Problem

It should be noted that because the aforementioned determination method using an optical microscope such as a phase contrast microscope is carried out by visually discriminating subtle differences in the cell shape, the results were easily affected by the subjective view and experience of the observer, and those subtle differences were easily overlooked. Also, although there is a confirmation method using fluorescent or luminescent labeling by introducing a reporter gene targeting the gene expression serving as an undifferentiation marker, this method requires the production of a human stem cell line stably expressing the reporter gene.

Also, there is a technique for confirming the presence of an undifferentiation marker such as the Alkaline Phosphatase (ALP) activity or a specific protein by dye color development or by using fluorescent antibodies after fixing stem cells. However, because stem cell culture cannot be continued according to this technique, the usage of this technique is limited merely to spot-check confirmation.

Solution to Problem

An observation method according to one aspect of the present invention comprises, placing stem cells in a transparent member, mounting the transparent member on a light guide member via an optical medium, emitting illumination light into the light guide member and emitting the illumination light to the stem cells in the transparent member containing a solution via the optical medium, and detecting scattered light, the scattered light being the illumination light emitted to the stem cells that is scattered by the stem cells and has passed through the light guide member.

In the observation method according to one aspect described above, illumination light that is emitted to stem cells is scattered by the stem cells, and the stem cells are observed by detecting the scattered light that has passed through the light guide member. According to the aforementioned observation method involving detecting scattered light that is scattered by the stem cells, the stem cells in the state tending toward differentiation can be displayed more darkly in comparison with an observation method involving detecting transmitted light that has passed through stem cells (for example, see FIG. 9 or FIG. 10). Thus, according to the observation method of the one aspect, the undifferentiated state and the state tending toward differentiation of stem cells can be distinguished while the stem cells are alive in culture, without labeling them, by a simple method employing scattered light.

Also, if no culture medium is required for observing stem cells, oblique illumination can be easily carried out without using a light guide member because of the refractive index; however, in order to observe stem cells, it is necessary to place them in a transparent member, and place a culture medium into the transparent member. According to the observation method of the one aspect described above, oblique illumination for observing stem cells can be easily obtained by using a light guide member and an optical medium.

The observation method according to the one aspect described above uses the intensity of scattered light as an index; therefore, as long as the two-dimensional information of the intensity distribution and the existing position of cell colonies are known, the undifferentiated state and the state tending toward differentiation of stem cells can be distinguished. Accordingly, it is possible to make a judgment by observing the entire container, which is the transparent member, or the area of light in the container at once using not only a microscope, but also a low magnification lens such as a macro lens.

In the observation method according to the one aspect described above, in the emitting the illumination light to the stem cells, it may also be possible to emit the illumination light to the stem cells diagonally relative to the direction of mounting of the transparent member on the light guide member. The emission angle of the above illumination light emitted diagonally to the stem cells may be between 53° and 90° relative to the direction of mounting. By the emission angle of the illumination light being in the aforementioned range, the contrast between a stem cell colony in the undifferentiated state and a stem cell colony in the state tending toward differentiation becomes clearer, making it even easier to distinguish between them.

In the observation method according to the one aspect described above, in the detecting the scattered light, it may also be possible to acquire images of the scattered light that is scattered by the stem cells and passed through the light guide member by an imaging unit. In order to obtain an intensity image of scattered light from cells at a high signal/noise ratio, dark-field illumination, etc. are generally carried out, and in order to do this, it is necessary to use a high NA condenser lens with a short differential distance under the microscope, and since the condenser lens needs to be brought close to the stem cells present in the transparent member, the operations were difficult. However, according to an observation method of one aspect of the present invention, a light guide member with a transparent member containing stem cells mounted thereon is used to obtain a scattered light image. Therefore, the image acquisition operation is made easy and intensity images of scattered light can be obtained at a high signal/noise ratio.

The observation method according to the one aspect described above may also be configured so as to further comprise, holding the transparent member by a holding mechanism, displaying the scattered light image obtained by the imaging unit by a display unit, receiving a selection input with respect to a certain cell region in the scattered light image displayed in the displaying and displaying a marker corresponding to the region thus selected on the image, removing the light guide member from under the transparent member after acquisition of the scattered light image of the stem cells, obtaining a transmitted light image of the stem cells by the imaging unit and displaying the transmitted light image by the display unit, and displaying the marker over the transmitted light image displayed in the displaying the transmitted light image.

In this case, the existing position of colonies can be known, irrespective of being differentiated or undifferentiated, on the transmitted light image. Also, since removing the light guide member from under the transparent member is included, the degree of freedom of access to the bottom surface side of the transparent member containing the stem cells can be increased. Further, for example, with respect to the cell colony identified in the scattered light image, it is possible to mark a certain area of the transparent member corresponding to the marker on the transmitted light image without transferring the transparent member containing the cells to another device. By doing so, the position of a stem cell colony in the state tending toward differentiation can be easily recognized.

After observing stem cells in the transparent member by the method for observing stem cells according to any of the aforementioned aspects, it is also possible to remove, from among the stem cells, a cell region that is identified as being in the state tending toward differentiation by the above observation. In this case, a stem cell colony in the undifferentiated state and a stem cell colony in the state tending toward differentiation can be easily distinguished with certainty, and based on such easy and certain distinction, a stem cell colony in the state tending toward differentiation can be removed, thereby enabling easy quality control of stem cells.

Further, an observation device according to one aspect of the present invention is an observation device for observing stem cells placed in a transparent member. This observation device comprises a light guide member having a surface on which the transparent member can be mounted, a first light source that emits illumination light into the light guide member and that emits the illumination light to the stem cells in the transparent member containing a solution via an optical medium disposed between the transparent member and the light guide member, a movement unit that moves the light guide member, a holding unit that holds the transparent member when the light guide member is moved by the movement unit, a second light source that emits illumination light to the stem cells placed in the transparent member held by the holding unit, and an imaging unit that images each of scattered light, the scattered light being the illumination light from the first light source that is scattered by the stem cells and has passed through the light guide member, and transmitted light, the transmitted light being the illumination light from the second light source that has passed through the stem cells.

According to the observation device of the one aspect described above, a scattered light image is easily obtainable by imaging scattered light that is scattered by stem cells, and as a result, the stem cells that are in the state tending toward differentiation, which are displayed darkly, can be easily identified. Thus, the undifferentiated state and the state tending toward differentiation of stem cells can be easily distinguished while the stem cells are alive in culture, without labeling them, by using the observation device according to the one aspect.

Advantageous Effects of Invention

According to one aspect of the present invention, the undifferentiated state and the state tending toward differentiation of stem cells can be easily distinguished while the stem cells are alive in culture, without labeling them. Also, according to one aspect of the present invention, the stem cells identified as being in the state tending toward differentiation can be removed as needed.

BRIEF DESCRIPTION OF DRAWINGS

FIG. 10 is a set of images of a mixture of other stem cells in the undifferentiated state and in the state tending toward differentiation, and (a) shows a scattered light image and (b) shows a transmitted light image.

DESCRIPTION OF EMBODIMENTS

Hereinbelow, the embodiments of the present invention will be described in detail with reference to the attached drawings. It is to be noted that the same symbols are used to denote the same elements or elements having the same function in the description, and redundant explanation is omitted.

[First Embodiment]

Figure 1:
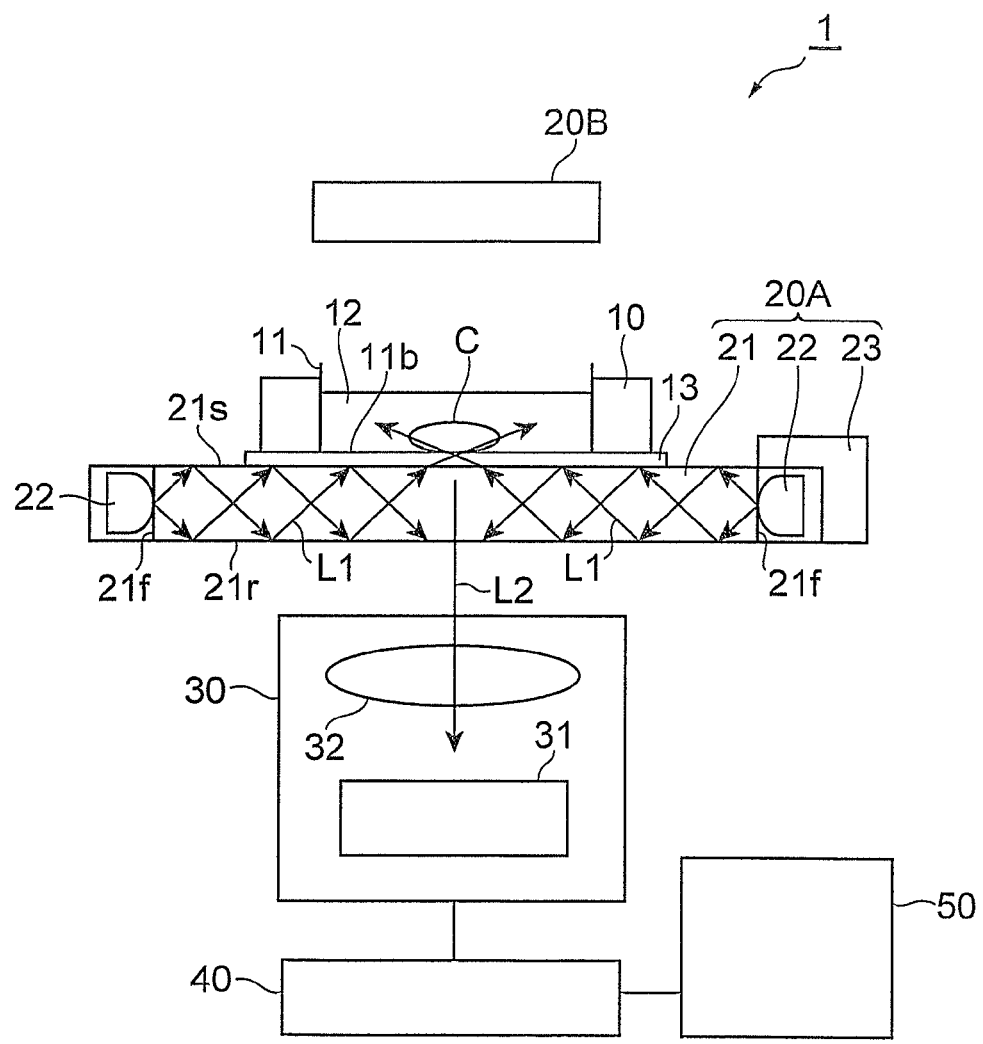
FIG. 1 is a diagram illustrating one embodiment of the observation device.
Figure 2:
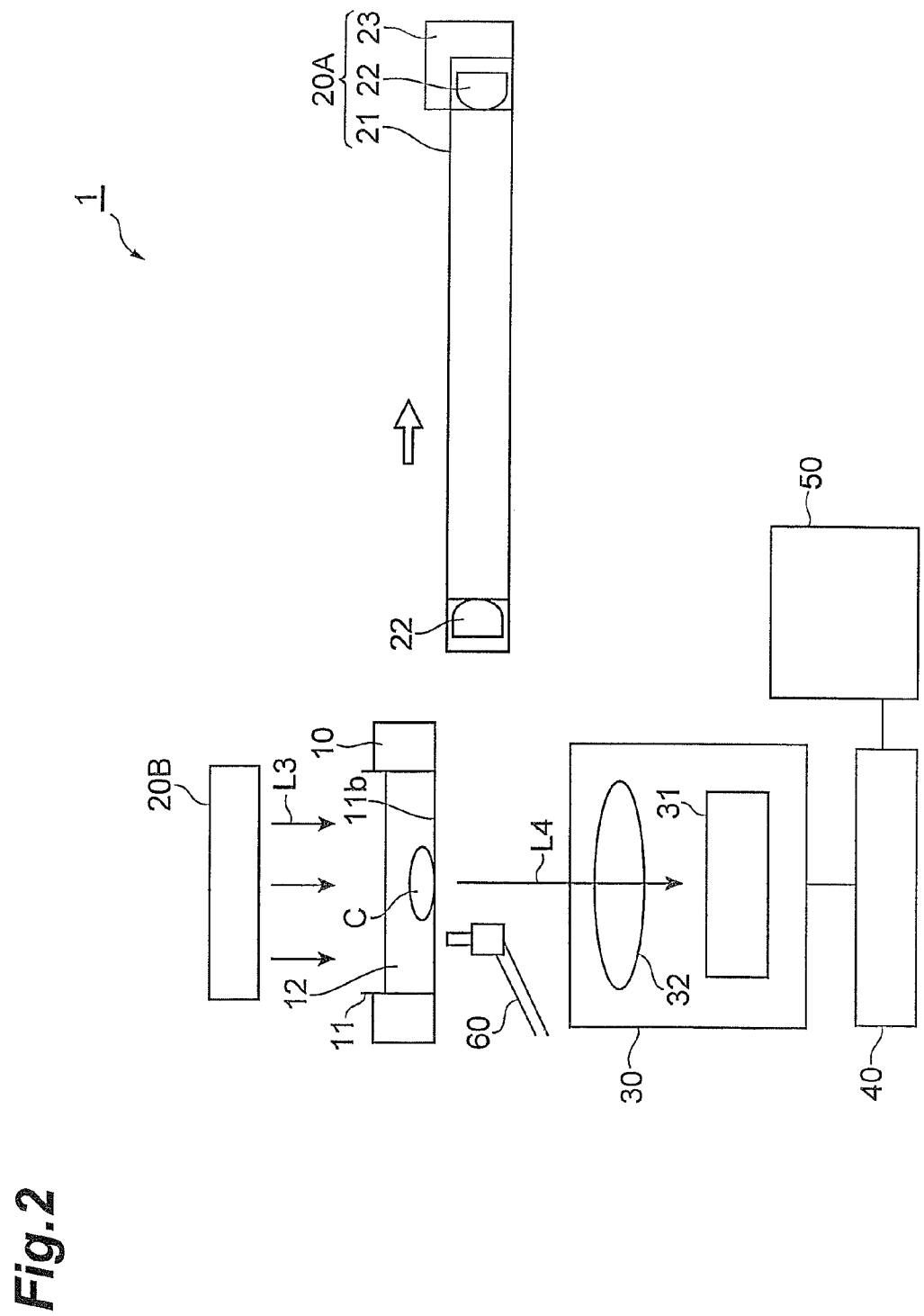
FIG. 2 is a diagram illustrating the state in which a waveguide is removed from a petri dish in the observation device illustrated in FIG. 1.

As illustrated in FIG. 1 and FIG. 2, an observation device 1 has a sample holding unit 10, light irradiation devices 20A and 20B, an image acquisition device 30, a control device 40, a display device 50, and a marking device 60.

The sample holding unit 10 is a member for holding the both ends of a petri dish 11, which is a transparent sample case. The bottom surface of the petri dish 11, to which, for example, iPS cells adhere, is composed of a light-transmitting member such as glass or plastic resin (such as polystyrene resin), and while it transmits illumination light L1 emitted from the light irradiation device 20A, it transmits scattered light L2 from human iPS cells C. A solution 12 such as culture medium is contained in the petri dish 11. Stem cells such as human iPS cells C are placed in the solution 12. A subset of the human iPS cells C adheres to a bottom surface 11b of the petri dish 11. It is to be noted that the bottom surface of a sample case, to which the stem cells adhere, may be formed of a light-transmitting member such as glass or polystyrene resin, and the sample case is not limited to a petri dish, and for example, a closed-system container connected to a fluid flow passage, the bottom surface of which is formed of a transparent member, may also be used.

The light irradiation device 20A has a waveguide 21, a light source device 22, and a moving device 23. The waveguide 21 and the light source device 22 in the light irradiation device 20A emit the illumination light L1 to the petri dish 11 containing the human iPS cells C. The waveguide 21 is a plate-like light guide member having a main surface 21s, a rear surface 21r, which is the opposite of the main surface 21s, and a side surface 21f, which is roughly orthogonal to the main surface 21s. The waveguide 21 is composed of a light-transmitting member such as quartz glass and has a thickness of approximately 3 mm to 8 mm. The petri dish 11 is mounted on the main surface 21s via water 13. Two light source devices 22 are disposed at both ends of the waveguide 21 in close proximity to the side surface 21f in such a manner that the direction of light emission is opposed to each other. The material of the waveguide 21 is not limited to quartz glass, and as long as a transparent material has a higher refractive index than air as glass, such a transparent material can be molded using resin. Also, although an example of using water as the optical medium is illustrated above, it is also possible to connect the waveguide 21 and the petri dish 11 by optical coupling using other optical media.

The light source device 22 is configured to include a light source unit. The light source unit of the light source device 22 has a configuration in which a plurality of LEDs (for example, red LED) are disposed in a frame member. A plurality of these LEDs emit directional illumination light L1 from the side surface 21f of the waveguide 21 into the waveguide 21. The light source device 22 may have an adjusting mechanism of the mounting angle of the light source unit so that the incident angle of light entering the waveguide 21 is adjusted. Also, the light source device 22 may be configured to further include a filter unit. The filter unit of the light source device 22 is, for example, a bandpass filter that only transmits light in a specific wavelength band. From the light emitted from LED, the filter unit only transmits illumination light L1 having an appropriate wavelength for measurement. As shown above, it becomes possible to emit light having an appropriate wavelength for measurement into the waveguide 21 by combining the light source unit and the filter unit, whereby measurement accuracy can be improved. In other words, wavelength selectivity can be improved by including the filter unit.

Figure 6:
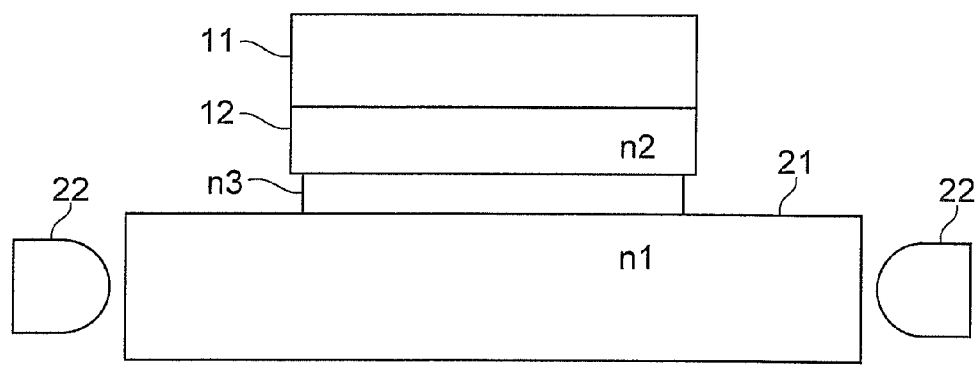
FIG. 6 is a diagram illustrating the state in which water is disposed between a waveguide and a petri dish.

The light irradiation device 20A emits the illumination light L1 into the petri dish 11 by setting a critical angle based on the refractive index n1 of the waveguide 21 and the refractive index n3 of the water 13, which is disposed on the main surface 21s of the waveguide 21, at a certain value. The optical medium, which is a means for emitting the illumination light L1 into the petri dish 11, is not limited to water as long as it fills the space between the waveguide and the bottom surface of the sample case, and for example, oil, glass, resin, and a gel-like substance can also be used. Further, it is also possible to emit the illumination light L1 into the petri dish 11 by setting the incident angle of the illumination light L1 relative to the main surface 21s at a certain value by forming a desired form such as a groove on the main surface 21s. The refractive index n3 of the optical medium (see FIG. 6) is preferably equivalent to or more than the refractive index n2 of the culture medium in the sample case, and if the refractive index n3 of the optical medium is larger than the refractive index n2 of the culture medium in the sample case, oblique illumination light can be emitted at a shallower angle.

The light source of the light source device 22 is not limited to the aforementioned LED. For example, as the light source of the light source device 22, a white light source such as a xenon lamp can also be used. In this case, the human iPS cells C can be irradiated with, as the illumination light L1, light having a wavelength that cannot be realized by LED. Also, although the example illustrated in FIG. 1 shows an example of mounting two light source devices 22, it is also possible to mount only one light source device 22 or three or more light source devices 22.

Figure 3:
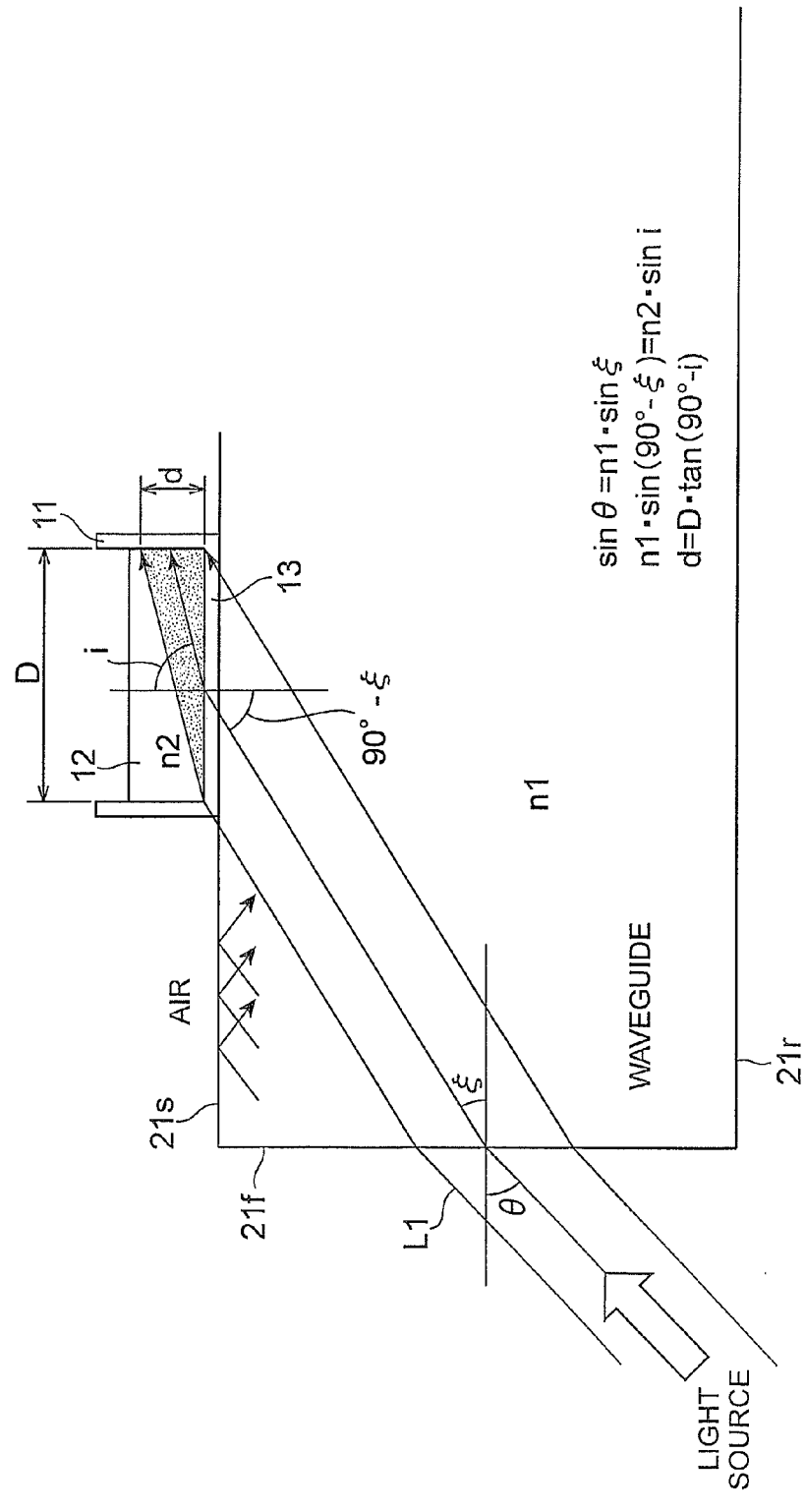
FIG. 3 is a diagram schematically illustrating the changes in the incident angle of light entering a petri dish from a light source.

At this point, the illumination light L1 in the light irradiation device 20A will be described in detail with reference to FIG. 3. FIG. 3 is a diagram schematically illustrating the changes in the incident angle of light entering the petri dish 11 from the light source 22. As illustrated in FIG. 3, the light irradiation device 20A emits the illumination light L1 containing light having a certain incident angle θ into the waveguide 21 from both side surfaces 21f of the waveguide 21. The illumination light L1 having the refractive index n1 higher than air that has entered the waveguide 21 undergoes total reflection by the main surface 21s and the rear surface 21r of the waveguide 21. Subsequently, a portion of the illumination light L1 enters the petri dish 11 through a region where the water 13 is disposed between the main surface 21s and the petri dish 11.

Figure 4:
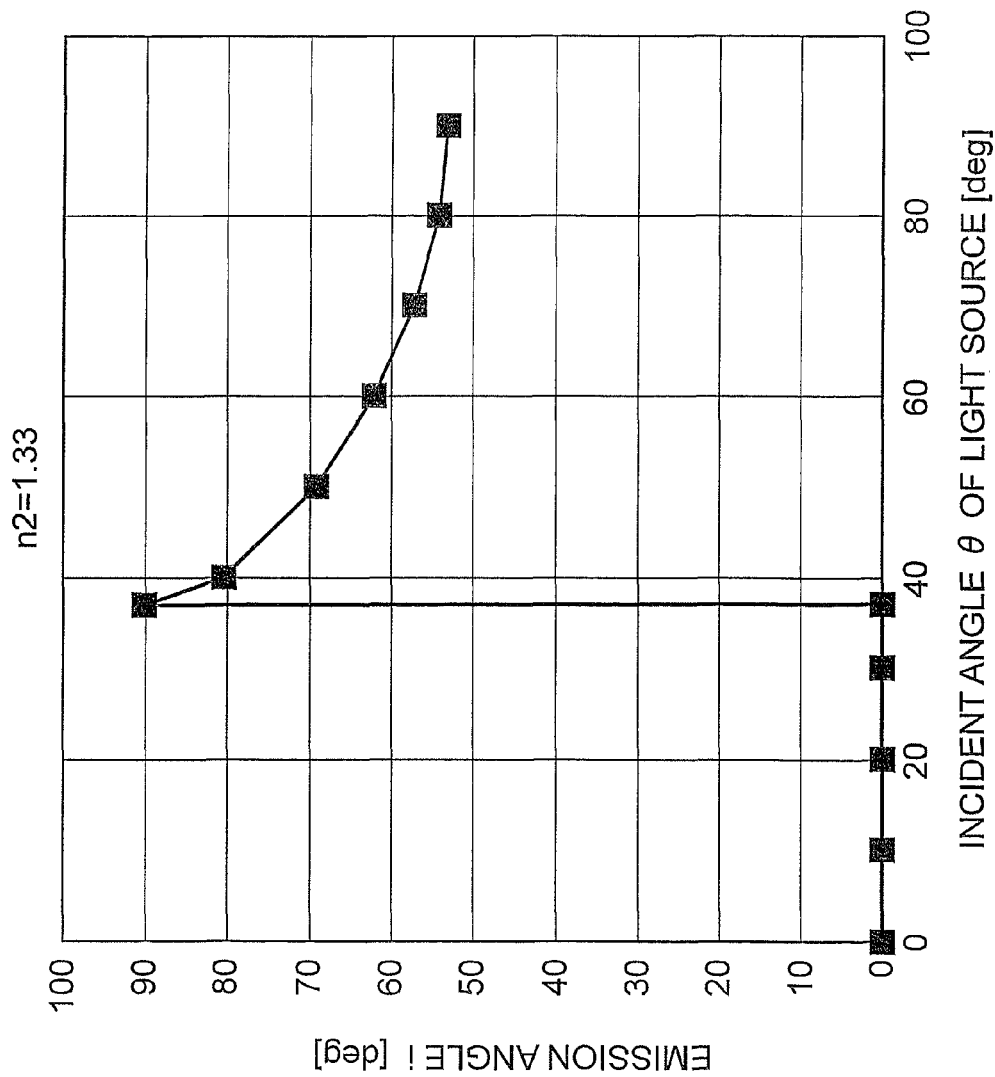
FIG. 4 is a diagram illustrating the relationship between the radiation angle from a light source and the emission angle to a petri dish.

The above illumination light L1 is refracted in the direction parallel to the main surface 21s due to differences between the refractive index n1 of the waveguide 21 and the refractive index n3 of the water 13, and emitted into the petri dish 11. The refractive index n2 of the solution 12 in the petri dish 11 is, for example, roughly equal to the refractive index of water. As a result, the illumination light L1 entering the petri dish 11 achieves a slope of a certain emission angle i relative to the direction of depth (direction of mounting) of the petri dish 11. For example, according to the example illustrated in FIG. 4, when the refractive index n2 of the solution 12 is 1.33, in the illumination light L1 emitted from the light source device 22 to the waveguide 21, incident light having an incident angle θ of approximately less than 37° undergoes total reflection without entering the petri dish 11 from the waveguide 21. Meanwhile, the illumination light L1 having an incident angle θ of approximately 37° or more (to be accurate, 37.03°) enters the culture medium 12 in the petri dish 11 at an emission angle i in the range of 53° to 90° relative to the direction of depth, whereby the human iPS cells C are irradiated with certain oblique illumination.

Figure 5:
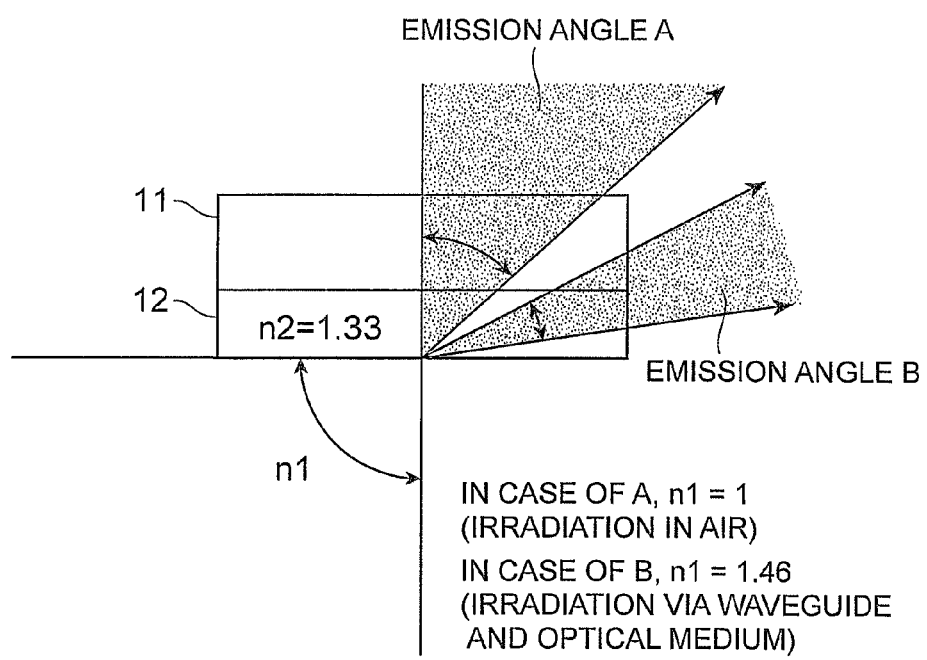
FIG. 5 is a diagram illustrating the differences between the emission angle to a petri dish with the use of a waveguide and the emission angle to a petri dish without the use of a waveguide.

As shown above, the light irradiation device 20A according to the present embodiment is configured so that light from the light source device 22 has a certain range of radiation angle (for example, 38° to 90°), and incident light emitted at such an angle θ enters into the petri dish 11 as oblique light further closer to parallel via the water 13 interposed between the waveguide 21 and petri dish 11. When the waveguide 21 and the like are not used, light enters the culture medium 12 from air, in accordance with the penetration of light from a refractive index of 1 to a refractive index of 1.33. In other words, as illustrated in FIG. 5, illumination light entering the petri dish 11 has an angle of less than 50° (the case of remission angle A) relative to the direction of depth of the petri dish 11. Meanwhile, by virtue of the aforementioned configuration, it is made possible to include light having an emission angle i in the range of 53° to 90° (the case of remission angle B) relative to the direction of depth of the petri dish 11 with the light irradiation device 20A.

The moving device 23 of the light irradiation device 20A is a transfer means for removing the waveguide 21 and the light source device 22 from under the petri dish 11 held by the sample holding unit 10. FIG. 2 illustrates the state in which the waveguide 21 and the light source device 22 are moved horizontally to the right from under the petri dish 11 by the moving device 23. The light irradiation device 20A positioned under the petri dish 11 is removed by this moving device 23, whereby the outer surface side of the bottom surface 11b of the petri dish 11 is made freely accessible.

The light irradiation device 20B is a second light source device configured to include a light source unit and a filter unit. As illustrated in FIG. 2, the light irradiation device 20B emits illumination light L3 to the petri dish 11 containing the human iPS cells C from above. The light source unit of the light irradiation device 20B is a light source for finding the existing position of cell colonies in the petri dish 11 and is composed of a LED light source and a condenser lens, and is configured to irradiate the observation area in the petri dish 11 or the entire petri dish 11 and emits directional illumination light L3 from above the petri dish 11. Similarly to the filter of the light source device 22, the filter unit of the light irradiation device 20B is, for example, a band-pass filter that only transmits light in a specific wavelength band. Although the light irradiation device 20B does not emit light while the light irradiation device 20A is emitting the illumination light L1, it may also be possible to allow the light irradiation device 20B to emit light when the light irradiation device 20A is positioned under the petri dish 11.

The image acquisition device 30 is a device for imaging the scattered light L2, which is the illumination light L1 from the light irradiation device 20A that is scattered by the human iPS cells C and has passed through the waveguide 21, and transmitted light L4, which is the illumination light L3 from the light irradiation device 20B that has passed through the human iPS cells C, and the image acquisition device 30 has an imaging device 31 and an image-forming lens 32. The imaging device 31 has a two dimensional pixel structure, in which a plurality of pixels are two-dimensionally arranged, and is configured to be capable of acquiring a scattered light image, which is a two-dimensional light detection image of the scattered light L2 from the human iPS cells C, and a transmitted light image, which is a two-dimensional light detection image of the transmitted light L4 from the human iPS cells C.

As the imaging device 31, for example, a high sensitivity CCD camera or CMOS imaging camera can be used. It may also be possible to configure the image acquisition device 30 by disposing an image intensifier tube, a relay lens, or the like in the front stage of the camera as needed. Also, the lens 32 is a lens for forming an image of the scattered light L2 and transmitted light L4 on the imaging device 31, and is disposed between the waveguide 21 and the imaging device 31. When necessary, an optical member such as an optical filter may be disposed between the waveguide 21 and the lens 32, or between the lens 32 and the imaging device 31. In order to prevent light emitted at an angle of oblique illumination from entering the observation side (i.e., the imaging device side), it is preferable to use a lens with low numerical aperture (light collection angle) as the lens 32. Acquisition of scattered light with good contrast is made possible by using such a lens with low numerical aperture.

The aforementioned image acquisition device 30 is disposed under the position where the petri dish 11 is mounted on the waveguide 21, and detects the scattered light L2 from the human iPS cells C in the petri dish 11. Then, the image acquisition device 30 detects a two-dimensional light image containing the scattered light L2 from the human iPS cells C contained in the petri dish 11 to acquire optical image data.

When the waveguide 21 and the like are moved from under the petri dish 11, the image acquisition device 30 detects the transmitted light L4, which is the transmitted light of the illumination light L3 emitted to the human iPS cells C in the petri dish 11. Subsequently, the image acquisition device 30 detects a two-dimensional light image containing the transmitted light L4 from the human iPS cells C contained in the petri dish 11 to acquire optical image data. The image acquisition device 30 may also acquire optical image data by detecting a two-dimensional light image containing the transmitted light L4 when the waveguide 21 and the like are present. The image acquisition device 30 outputs the optical image data thus obtained to a control device 40.

Figure 9:
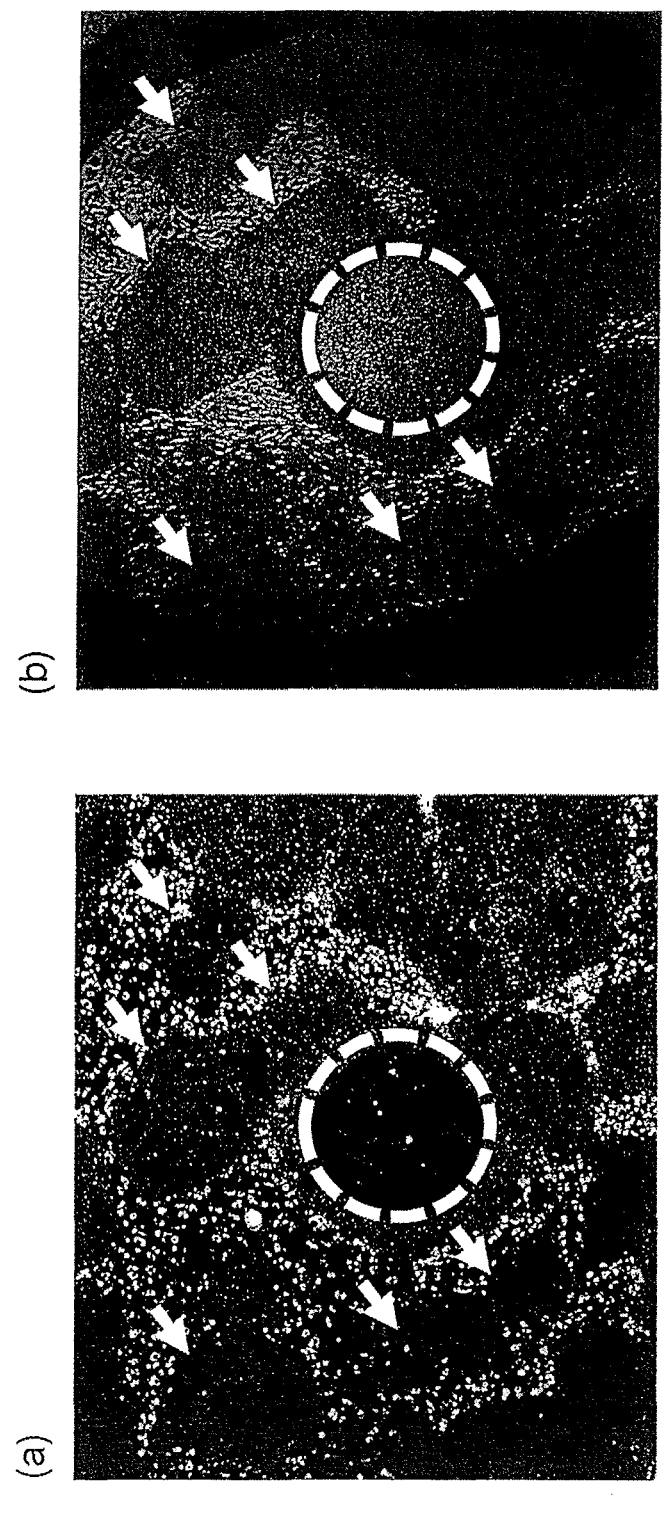
FIG. 9 is a set of images of a mixture of stem cells in the undifferentiated state and in the state tending toward differentiation, and (a) shows a scattered light image and (b) shows a transmitted light image.

The control device 40 is connected to the image acquisition device 30 and displays the optical image data input by the image acquisition device 30 as a scattered light image or a transmitted light image as illustrated in FIG. 9 and FIG. 10 on the display device 50. The control device 40 is composed of, for example, a personal computer with CPU that executes processing and controlling by software, and the display device 50 is composed of, for example, a display. FIG. 9 (a) and FIG. 10 (a) each show scattered light images of the human iPS cells C and FIG. 9 (b) and the FIG. 10 (b) each show transmitted light images of the human iPS cells C displayed by the control device 40 and the display device 50. In the scattered light images shown in FIG. 9 (a) and FIG. 10 (a), the area surrounded by a dotted circle indicates a cell colony in the state tending toward differentiation, and the cell colony in the state tending toward differentiation is shown much more darkly than the surrounding cell colonies in the undifferentiated state (such as those indicated by arrows in FIG. 9).

Figure 7:
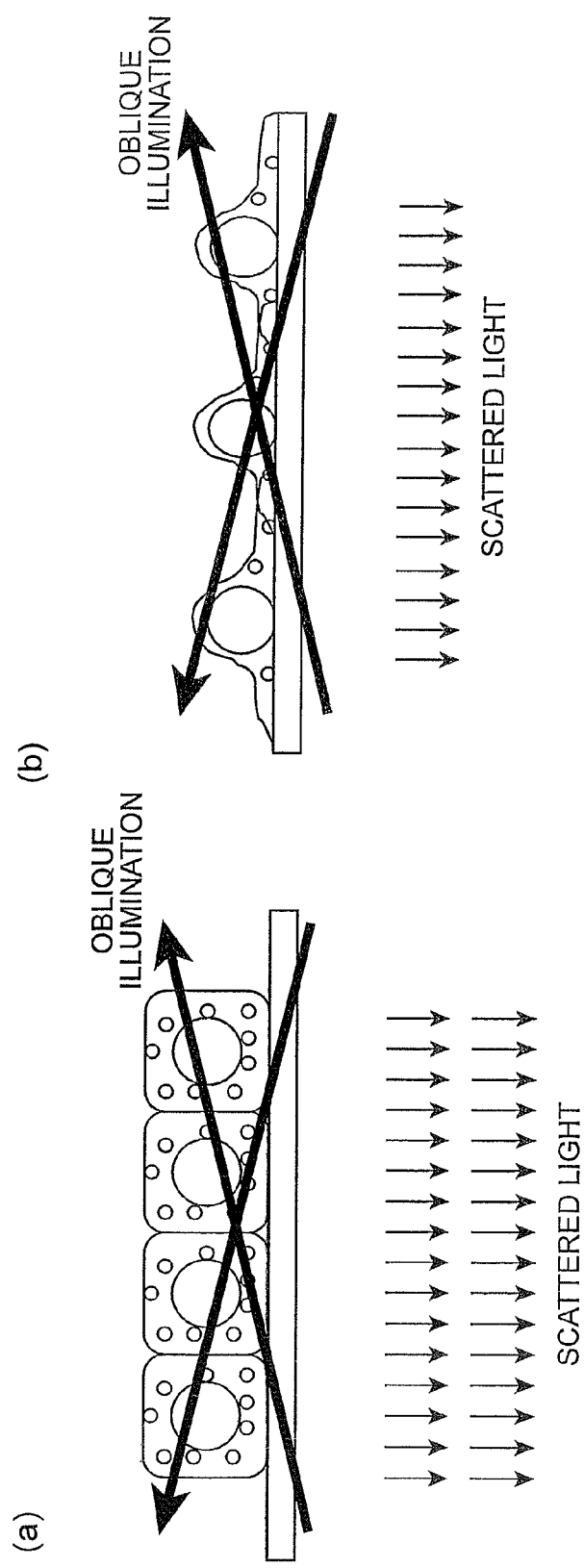
FIG. 7 is a set of diagrams illustrating the relationship between oblique illumination and the intensity of scattered light in stem cells, and (a) illustrates the relationship in the stem cells in the undifferentiated state and (b) illustrates the relationship in stem cells in the state tending toward differentiation.
Figure 8:
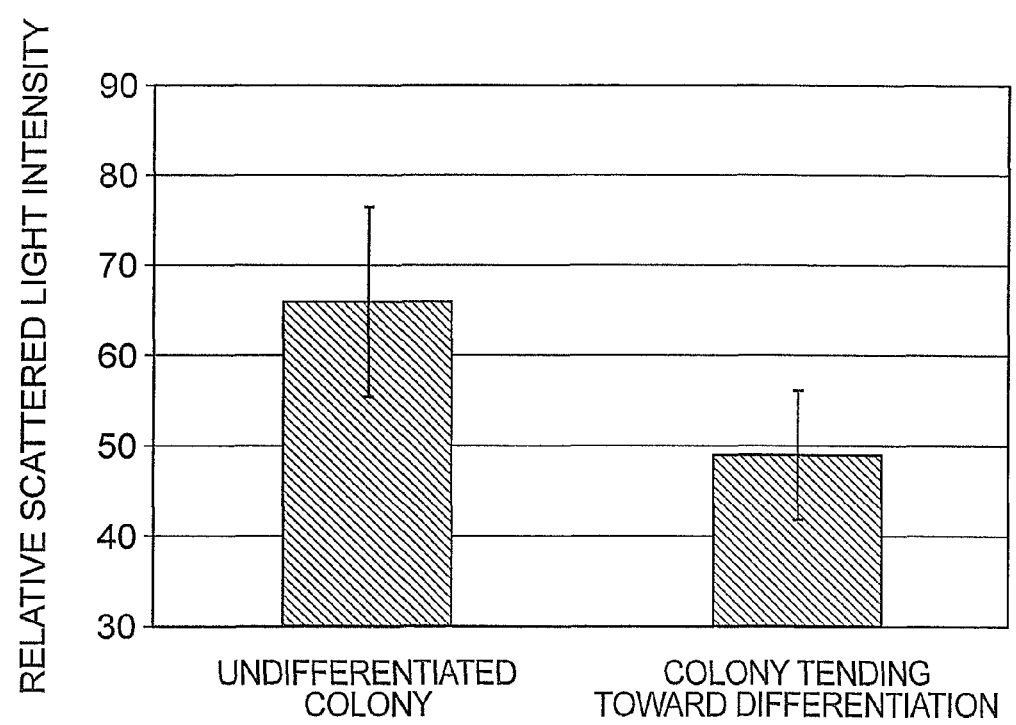
FIG. 8 is a diagram illustrating the intensity of scattered light in stem cell colonies.

At this point, the mechanism by which the cell colony in the state tending toward differentiation is shown more darkly than the cell colony in the undifferentiated state will be described with reference to FIG. 7 and FIG. 8. According to the present inventors, as illustrated in FIG. 7, it is presumed that each cell becomes thinner in thickness or the intracellular structure, which is responsible for generating scattered light, is reduced in amount in a cell colony in the state tending toward differentiation (FIG. 7 (b)) in comparison with a cell colony in the undifferentiated state (FIG. 7 (a)). When each cell constituting a cell colony is thick in thickness or the intracellular structure, which is responsible for generating scattered light, is large in amount, the rate of reflection of the illumination light L1 entering as oblique illumination as scattered light becomes high, resulting in a brighter light image with strong scattered light intensity. However, when the cells in a cell colony are thin in thickness as described above, the rate of reflection of the illumination light L1 entering as oblique illumination as scattered light becomes low, resulting in weak scattered light intensity. In consequence, it is presumed that a cell colony in the state tending toward differentiation is displayed as a darker light image.

As described above, the present embodiment employs a scattered light image, thereby clarifying the differences between the differentiated state and the undifferentiated state. As illustrated in FIG. 9 (b) and FIG. 10 (b), differences between the differentiated state and the undifferentiated state are not very distinct in a transmitted light image, and without an identification mark in the corresponding scattered light image, it is difficult to distinguish between the differentiated state and the undifferentiated state in a transmitted light image.

The control device 40 receives certain marking input by an input device (not shown) such as a mouse or a tablet, and as illustrated in FIG. 9 (a) and the like, performs processing of displaying the content of the marking (for example, the dotted circles or arrows) on a scattered light image according to the content of the marking input. The control device 40 holds the coordinate position of the marking as data and displays the content of the marking again on a transmitted light image displayed after the scattered light image. Because the scattered light image and the transmitted light image are displayed in such a way that their coordinate positions correspond to each other by controlling their positions by the control device 40 and the like, the cell colony in the state tending toward differentiation can be identified by confirming the marking on the transmitted light image.

The marking device 60 is a member for making a certain mark on the outer surface of the bottom surface 11b of the petri dish 11. The marking device 60 has, for example, an ink pen capable of making a mark corresponding to the marked spot (dotted circle) shown in FIG. 9 (b) on the outer surface of the bottom surface 11b of the petri dish 11 according to the operation of the observer.

Figure 11:
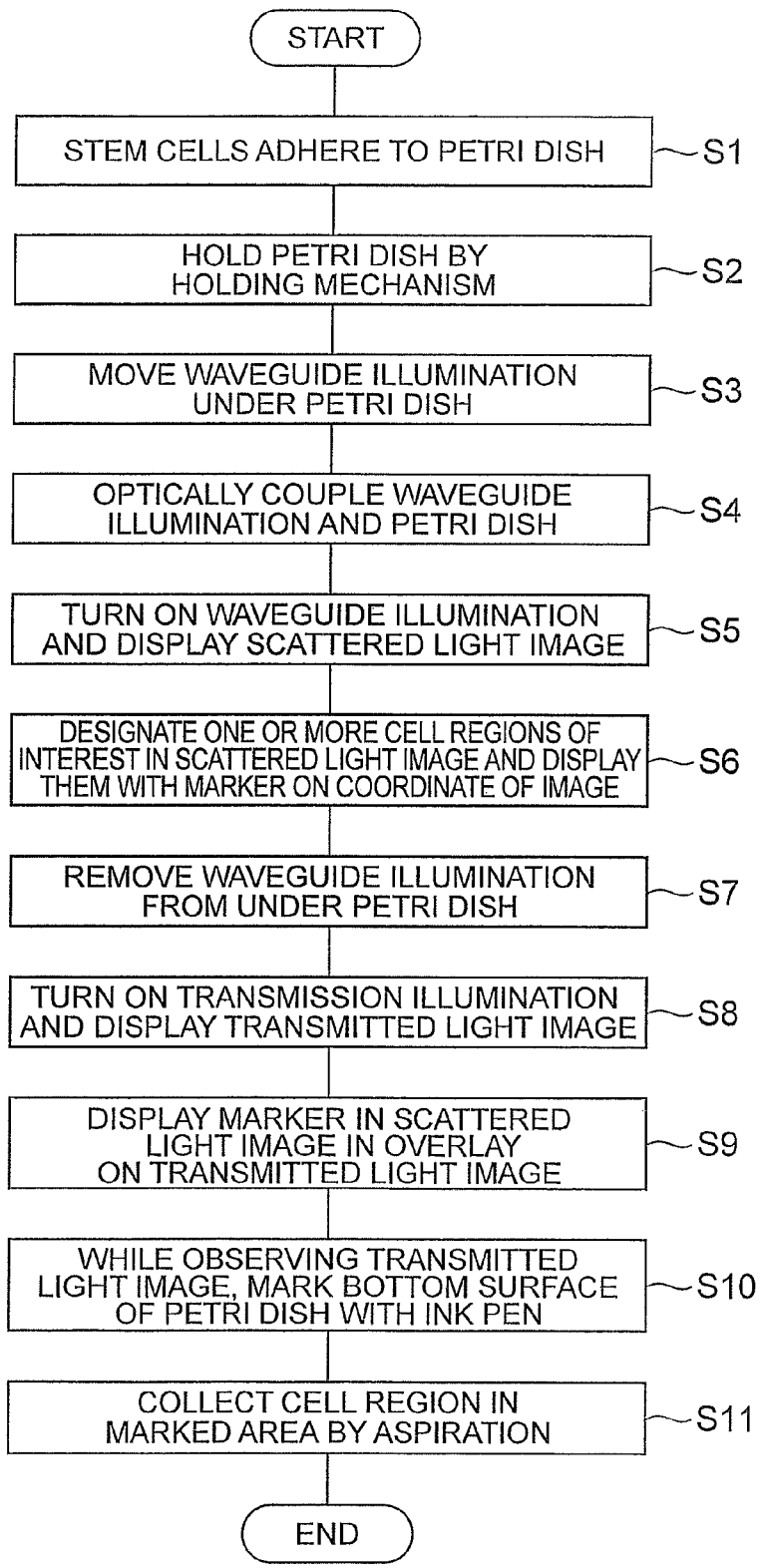
FIG. 11 is a flowchart illustrating a first embodiment of the observation method for observing stem cells with the observation device illustrated in FIG. 1 and FIG. 2.

Subsequently, an observation method using the aforementioned observation device 1 will be described with reference to FIG. 11.

First of all, a petri dish 11 containing a solution 12 such as culture medium is prepared, and stem cells C such as human iPS cells are allowed to adhere to the bottom surface of the petri dish 11 (step S1). Further, the petri dish 11 is held by a sample holding unit 10, which is the holding mechanism (step S2). It may be possible to allow the sample holding unit 10 to hold the petri dish 11 after the stem cells C adhere to the petri dish 11, or allow the stem cells C to adhere to the petri dish 11 that is held by the sample holding unit 10.

Subsequently, the waveguide 21 or the petri dish 11 is moved so that the waveguide 21 of the light irradiation device 20 A is located under the petri dish 11 (step S3), and water 13 is applied to a certain area of the main surface 21s of the waveguide 21, and the petri dish 11 is mounted on the waveguide 21 via the water 13. As a result, the arrangement configuration illustrated in FIG. 1 is achieved and the waveguide 21 and the petri dish 11 are optically coupled (step S4).

Subsequently, the power supply device 22 in the light irradiation device 20A is turned on to emit the illumination light L1 into the waveguide 21 (step S5). The illumination light L1 entering the waveguide 21 is refracted in the direction parallel to the main surface 21s in the area where the water 13 is interposed due to differences in the refractive index between the waveguide 21 and the water 13 while repeatedly undergoing total reflection in the waveguide 21, and then emitted into the petri dish 11. The illumination light L1 entering the petri dish 11 has a slope of a certain angle i relative to the direction of depth (direction of mounting) of the petri dish 11 (see FIG. 3).

The oblique illumination light L1 emitted into the petri dish 11 is scattered by the stem cells C and becomes scattered light and passes through the waveguide 21. A scattered light image is acquired by obtaining this scattered light L2 by the image acquisition device 30, and as illustrated in FIG. 12 (*a*), the scattered light image is displayed on the display device 50 by the control device 40 (step S5).

Figure 12:
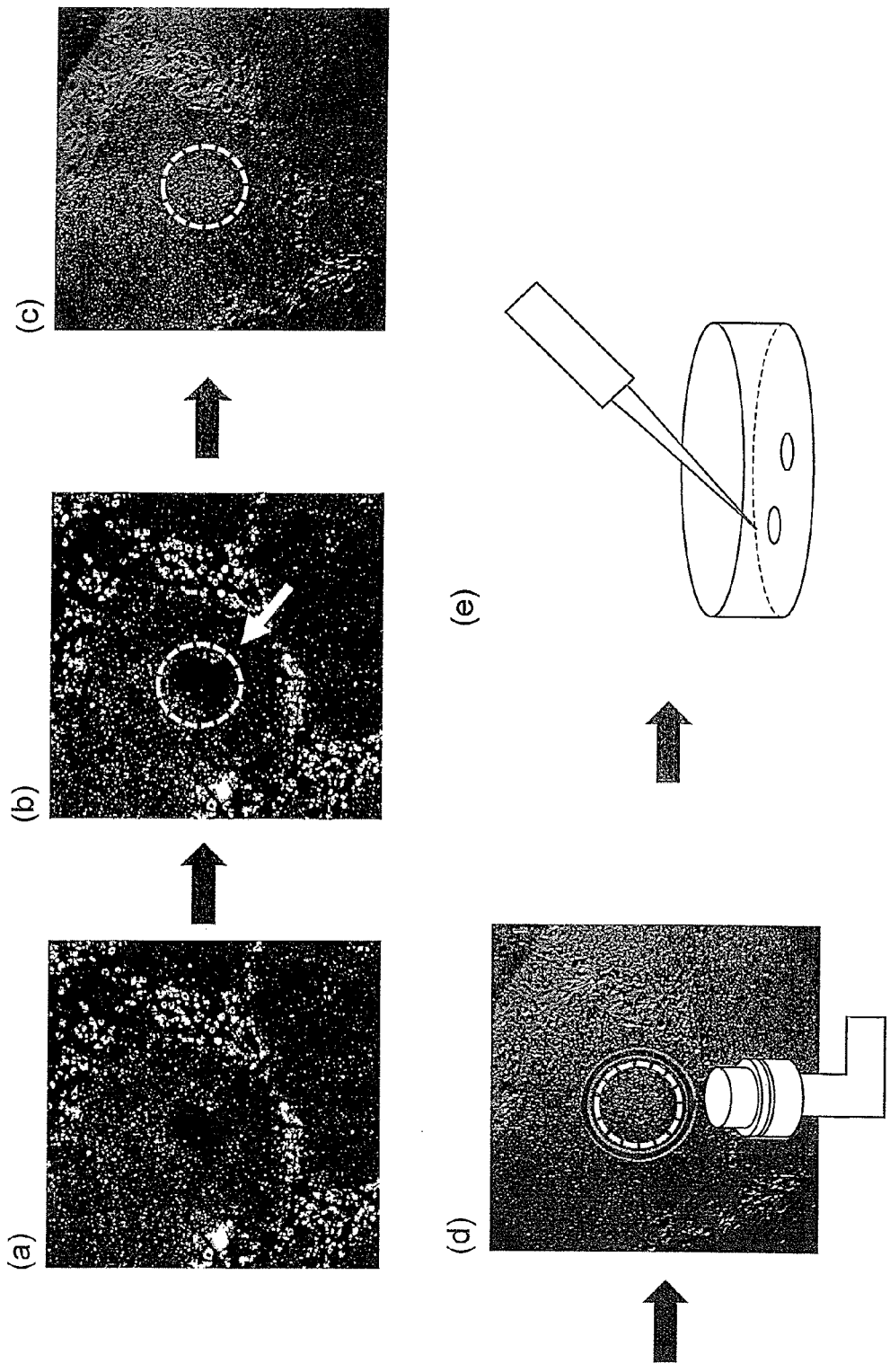
FIG. 12 is a set of diagrams illustrating the transition of images according to the observation method illustrated in FIG. 11.

Subsequently, the scattered light image displayed on the display device 50 is observed and one or more cell regions in the state tending toward differentiation are designated and displayed with a marker (a dotted circle) on the coordinate of the image as illustrated in FIG. 12 (*b*) (step S6). Since a cell region in the state tending toward differentiation is shown much more darkly than other cell regions in the undifferentiated state in a scattered light image as mentioned above, making it easier to distinguish between the differentiated state and the undifferentiated state.

After acquisition of the scattered light image, as illustrated in FIG. 2, the waveguide 21 is moved horizontally to the right by the moving device 23, whereby the waveguide 21 is removed from under the petri dish 11 (step S7). Subsequently, the process proceeds to step S8, and the power supply device of the irradiation device 20B is turned on and the petri dish 11 is irradiated with the illumination light L3. Subsequently, the illumination light L3 emitted to the petri dish 11 passes through the stem cells C and becomes the transmitted light L4. A transmitted light image is acquired by obtaining this scattered light L4 by the image acquisition device 30, and as illustrated in FIG. 12 (*c*), the transmitted light image is displayed on the display device 50 by the control device 40 (step S8).

Subsequently, while keeping this transmitted light image displayed, the marker displayed in the step S6 is retrieved from the control device 40 and displayed in overlay on the transmitted light image as illustrated in FIG. 12 (*c*) (step S9). Since the scattered light image displayed in the step S5 and the transmitted light image displayed in the step S9 are controlled by the control device 40 so that their coordinate positions correspond to each other, the marker displayed in overlay on the transmitted light image indicates the cell colony in the state tending toward differentiation.

Subsequently, while observing the transmitted light image shown in FIG. 12 (*c*), the outer surface of the bottom surface 11b of the petri dish 11 is marked with the ink pen of the marking device 60 so that the mark overlaps the marker on the transmitted light image as illustrated in FIG. 12 (*d*) (step S10). After that, as illustrated in FIG. 12 (*e*), the cell colony in the state tending toward differentiation is removed by collecting the cell colony in the marked area by aspiration using a dropper applicator and the like (step S11).

As described above, according to the observation method of the present embodiment, the stem cells C in the state tending toward differentiation can be displayed more darkly compared to the observation method involving detecting transmitted light passing through the stem cells C (see, for example, FIG. 9 and FIG. 10). Thus, according to the present observation method, the undifferentiated state and the state tending toward differentiation of stem cells C can be distinguished while the stem cells C are alive in culture, without labeling them, by a simple method employing scattered light.

In the aforementioned observation method, the intensity of the scattered light L2 is used as an index; therefore, as long as the two-dimensional information of the intensity distribution and the existing position of cell colonies are known, the undifferentiated state and the state tending toward differentiation of stem cells can be distinguished. Accordingly, it is possible to make a judgment by observing the entire petri dish 11, which is the transparent member, or the area of light in the petri dish 11 at once using not only a microscope, but also a low magnification lens such as a macro lens.

In the aforementioned observation method, the illumination light L1 irradiating the stem cells C is emitted diagonally relative to the direction of depth of the petri dish 11. The emission angle i of the illumination light L1 diagonally emitted to the stem cells C is between 53° and 90° relative to the direction of depth. By the emission angle i of the illumination light L1 being within the aforementioned range, the contrast between a stem cell colony in the undifferentiated state and a stem cell colony in the state tending toward differentiation becomes clearer, making it even simpler to distinguish between them.

In the aforementioned observation method, the image of the scattered light L2, which is scattered by the stem cells C and has passed through the waveguide 21, is acquired by the image acquisition device 30. In order to obtain an intensity image of scattered light from cells at a high signal/noise ratio, dark-field illumination, etc. are generally carried out, and in order to do this, it is necessary to use a high NA condenser lens with a short differential distance under the microscope, and these operations were difficult. However, according to this observation method, the waveguide 21 with the petri dish 11 containing the stem cells C mounted thereon is used to obtain a scattered light image. Therefore, the image acquisition operation is made easy and intensity images of scattered light can be obtained at a high signal/noise ratio.

In the aforementioned observation method, when the transmitted light image is displayed, the marker of the scattered light image is displayed in overlay on the transmitted light image. As a result, a stem cell colony in the undifferentiated state and a stem cell colony in the state tending toward differentiation are easily distinguished on the transmitted light image, making culture operations easy. Also, since a step of removing the waveguide 21 from under the petri dish 11 is included, the degree of freedom of access to the bottom surface side of the petri dish 11 containing the stem cells C can be increased. Further, for example, with respect to the cell colony identified in the scattered light image, it is possible to mark a certain area of the petri dish corresponding to the marker on the transmitted light image without transferring the petri dish 11 containing the cells to another device. By doing so, the position of a stem cell colony in the state tending toward differentiation can be easily recognized.

In the aforementioned embodiment, the stem cells C on the petri dish 11 are observed by the aforementioned method for observing stem cells, and based on the observation thus made, from among the stem cells C, the cell region identified as being in the state tending toward differentiation is removed. As a result, a stem cell colony in the undifferentiated state and a stem cell colony in the state tending toward differentiation can be easily distinguished with certainty, and based on such easy and certain distinction, a stem cell colony in the state tending toward differentiation can be removed, thereby enabling easy quality control of stem cells.

According to the observation device 1, a scattered light image can be easily obtained by imaging the scattered light L2, which is scattered by the stem cells C, and the stem cells C that are in the state tending toward differentiation, which are displayed darkly, can be easily identified. As a result, the undifferentiated state and the state tending toward differentiation of the stem cells C can be easily distinguished while the stem cells are alive in culture, without labeling them, by using the observation device 1.

Figure 13:
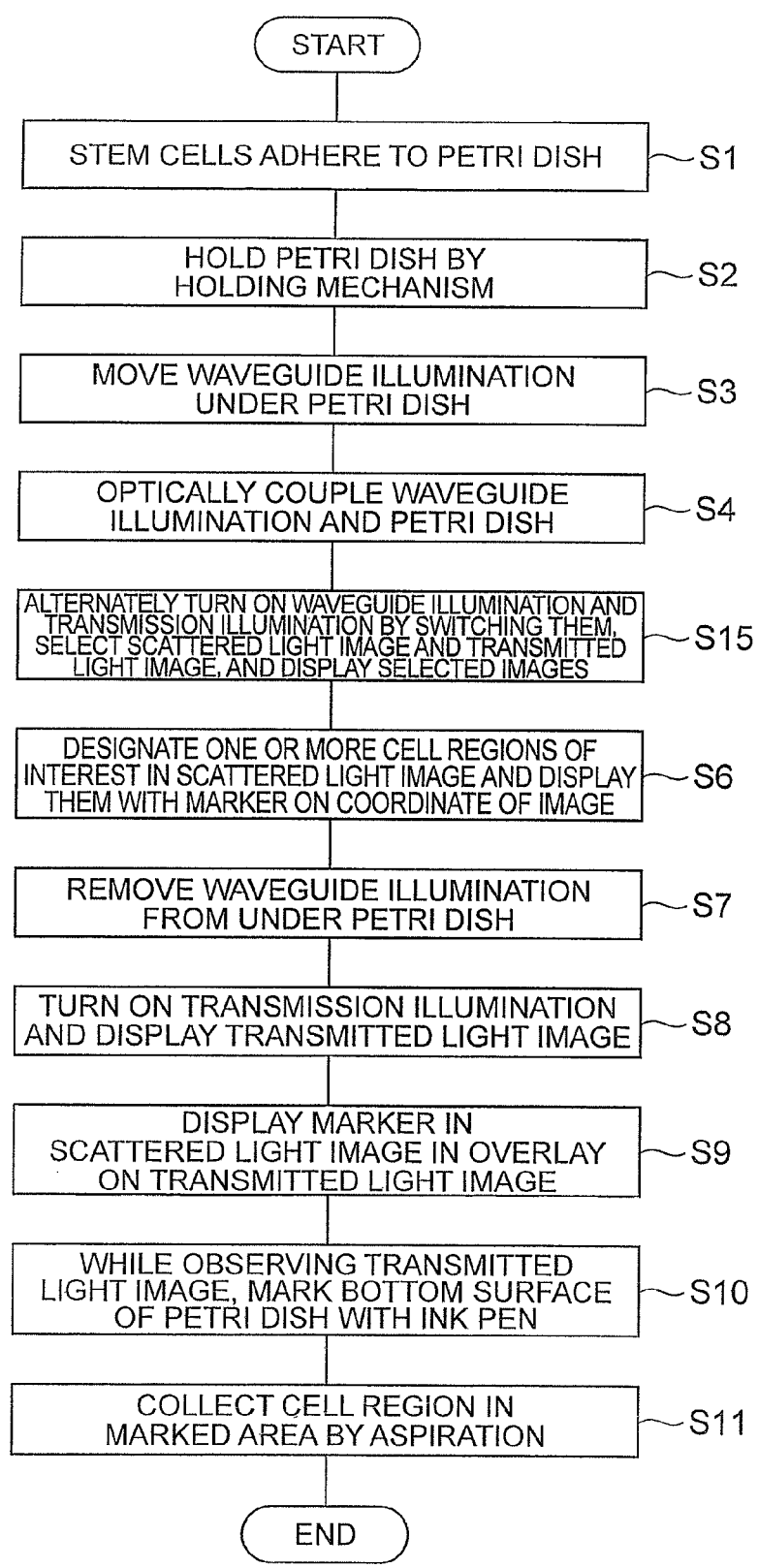
FIG. 13 is a flowchart illustrating a modification example of the observation method illustrated in FIG. 11.

According to the aforementioned embodiment, the transmitted light image is displayed after the scattered light image is displayed; however, for example, as illustrated in FIG. 13, it is also possible to alternately turn on the light irradiation devices 20A and 20B by switching them and select a scattered light image and a transmitted light image, and display selected images on the display device 50 (step S15). As shown above, it is made even easier for the observer to recognize the position of a cell colony in the state tending toward differentiation in a transmitted light image by alternately displaying both images when the scattered light image is displayed. The modification example of the observation method illustrated in FIG. 13 is the same as the observation method illustrated in FIG. 12, except for the step 15.

[Second Embodiment]

Figure 14:
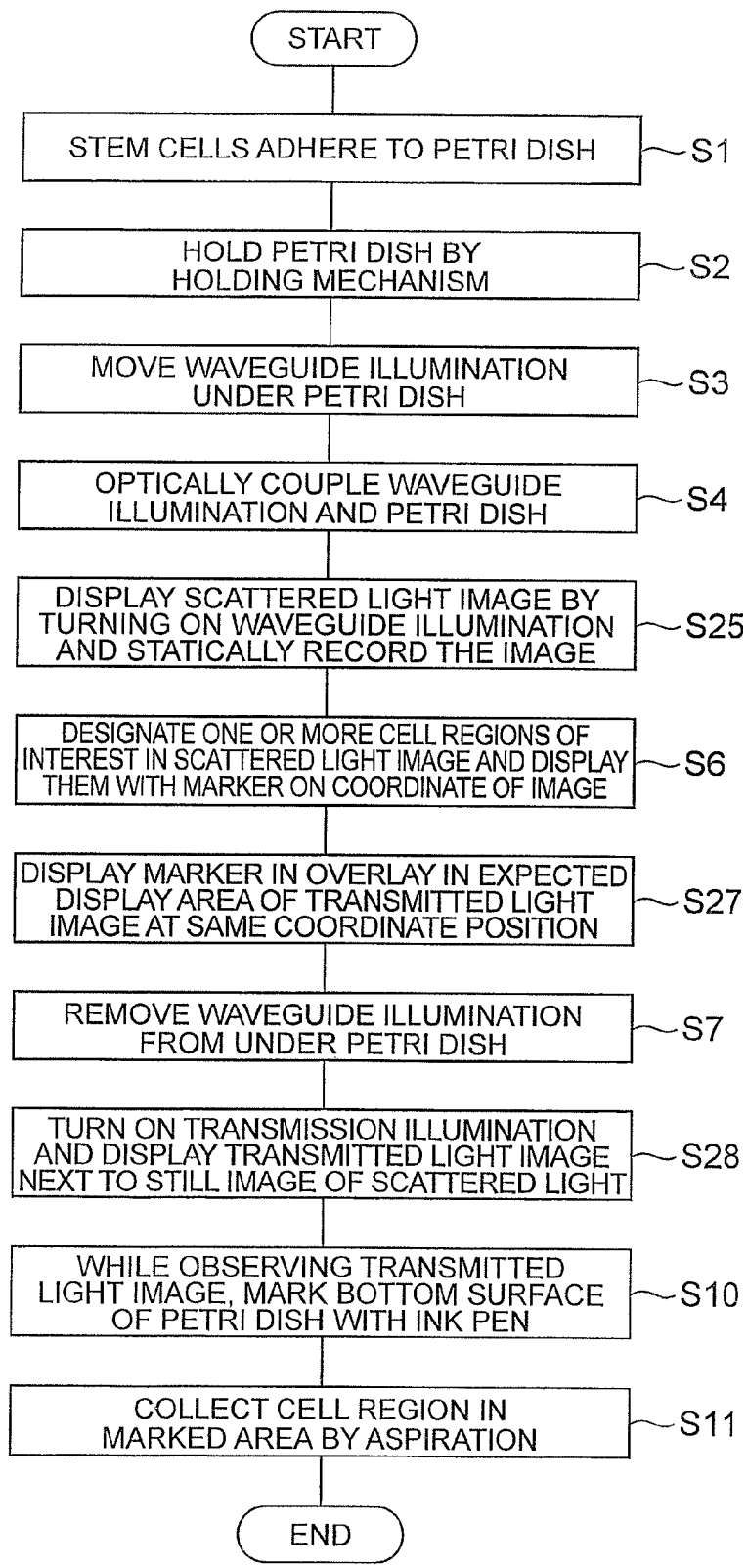
FIG. 14 is a flowchart illustrating a second embodiment of the observation method for observing stem cells with the observation device illustrated in FIG. 1 and FIG. 2.

Subsequently, a second embodiment of the observation method will be described with reference to FIG. 14 and FIG. 15. In the present embodiment, observation is performed with the observation device 1 as in the first embodiment. Hereinbelow, the observation method will be described, focusing on the differences from the first embodiment.

First of all, a petri dish 11 containing a solution 12 such as culture medium is prepared, and stem cells C such as human iPS cells are allowed to adhere to the bottom surface of the petri dish 11 (step S1). Further, the petri dish 11 is held by the sample holding unit 10, which is the holding mechanism (step S2). Subsequently, the waveguide 21 or the petri dish 11 is moved so that the waveguide 21 of the light irradiation device 20A is located under the petri dish 11 (step S3), and water 13 is applied to a certain area of the main surface 21s of the waveguide 21, and the petri dish 11 is mounted on the waveguide 21 via the water 13 so that the waveguide 21 and the petri dish 11 are optically coupled (step S4).

Subsequently, the power supply device 22 in the light irradiation device 20A is turned on to emit the illumination light L1 into the waveguide 21. The illumination light L1 entering the waveguide 21 is refracted in the direction parallel to the main surface 21s in the area where the water 13 is interposed while repeatedly undergoing total reflection in the waveguide 21, and then emitted into the petri dish 11. The oblique illumination light L1 emitted into the petri dish 11 is scattered by the stem cells C and becomes the scattered light L2, and passes through the waveguide 21. A scattered light image is acquired by obtaining this scattered light L2 by the image acquisition device 30, and as illustrated in FIG. 15 (a), the scattered light image is displayed on the display device 50 (step S25). Also, the control device 40 records the above image data as a still image (step S25).

Figure 15:
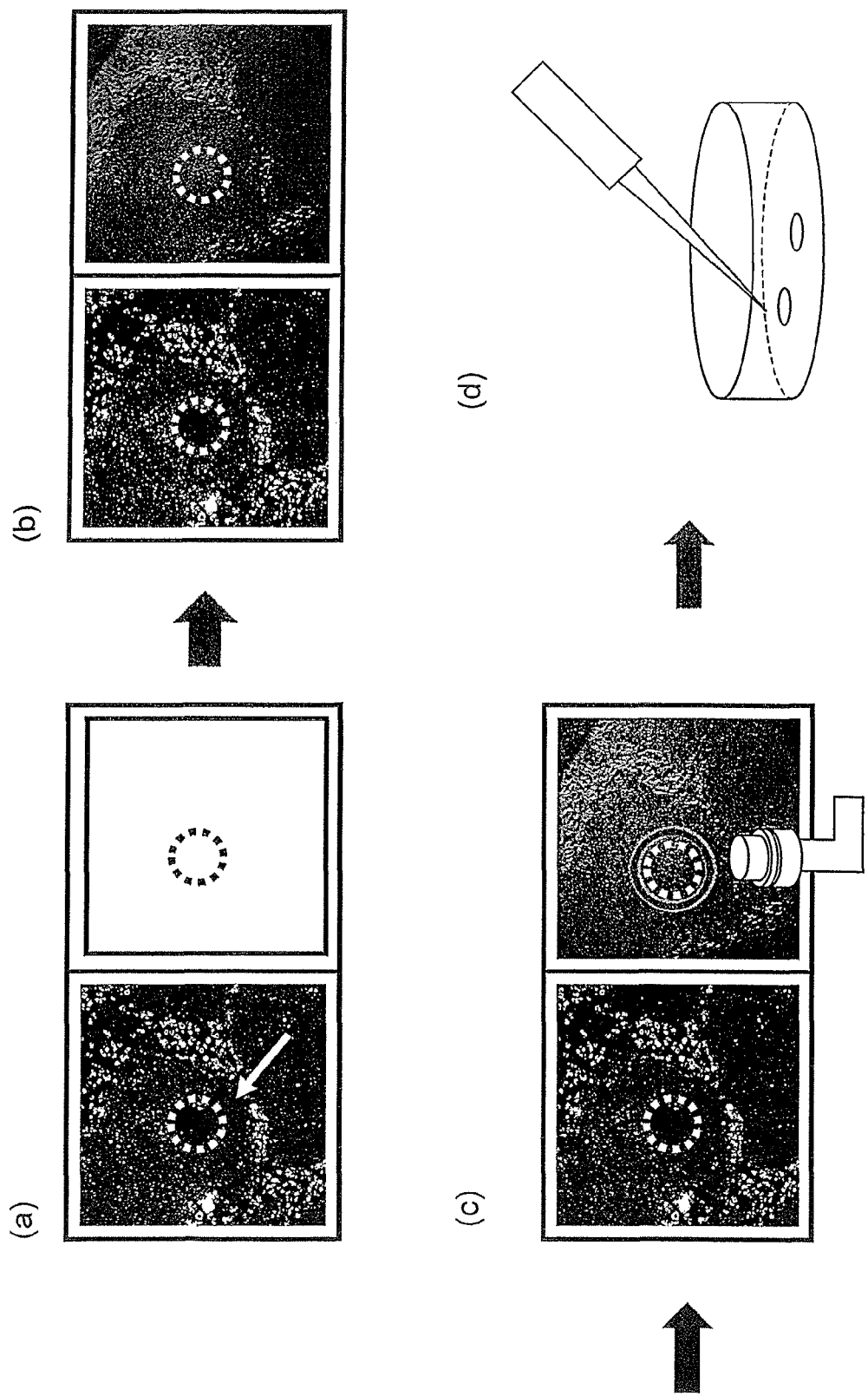
FIG. 15 is a set of diagrams illustrating the transition of images according to the observation method illustrated in FIG. 14.

Subsequently, the scattered light image displayed on the display device 50 is observed and one or more cell regions in the state tending toward differentiation are designated and displayed with a marker (a dotted circle) on the coordinate of the image as illustrated in FIG. 15 (a) (step S6). Since the cell colony in the state tending toward differentiation is shown much more darkly than other cell regions in the undifferentiated state in a scattered light image as mentioned above, the differentiated state and the undifferentiated state is easily distinguished. After that, as illustrated in FIG. 15 (a), the marker displayed in the step S6 is displayed in the expected display area of the transmitted light image (the right side of the Figure) at the same coordinate position in overlay (step S27).

After acquisition of the scattered light image, as illustrated in FIG. 2, the waveguide 21 is moved horizontally to the right by the moving device 23, whereby the waveguide 21 is removed from under the petri dish 11 (step S7). Subsequently, the process proceeds to step S28, and the power supply device of the irradiation device 20B is turned on and the petri dish 11 is irradiated with the illumination light L3. Subsequently, a transmitted light image is acquired by obtaining the transmitted light L4, which is the illumination light L3 emitted to the petri dish 11 that has passed through the stem cells C, by the image acquisition device 30, and as illustrated in FIG. 15 (b), the transmitted light image is displayed next to the still image of scattered light by the control device 40 (step S28).

Subsequently, while observing the transmitted light image shown in FIG. 15 (b), the outer surface of the bottom surface 11b of the petri dish 11 is marked with the ink pen of the marking device 60 so that the mark overlaps the marker on the transmitted light image as illustrated in FIG. 15 (c) (step S10). After that, as illustrated in FIG. 15 (d), the cell colony in the state tending toward differentiation is removed by collecting the cell colony in the marked area by aspiration using a dropper applicator and the like (step S11).

As described above, according to the observation method of the present embodiment, the stem cells C in the state tending toward differentiation can be displayed more darkly compared to the observation method involving detecting transmitted light passing through the stem cells C (see, for example, FIG. 9 and FIG. 10). Thus, according to the present observation method, the undifferentiated state and the state tending toward differentiation of stem cells C can be distinguished while the stem cells C are alive in culture, without labeling them, by a simple method employing scattered light.

In the aforementioned observation method, the scattered light image is displayed next to the transmitted light image as a still image. Thus, the position of the cell colony in the state tending toward differentiation can be identified on the transmitted light image while referring to the scattered light image, making identification operations much easier.

Figure 16:
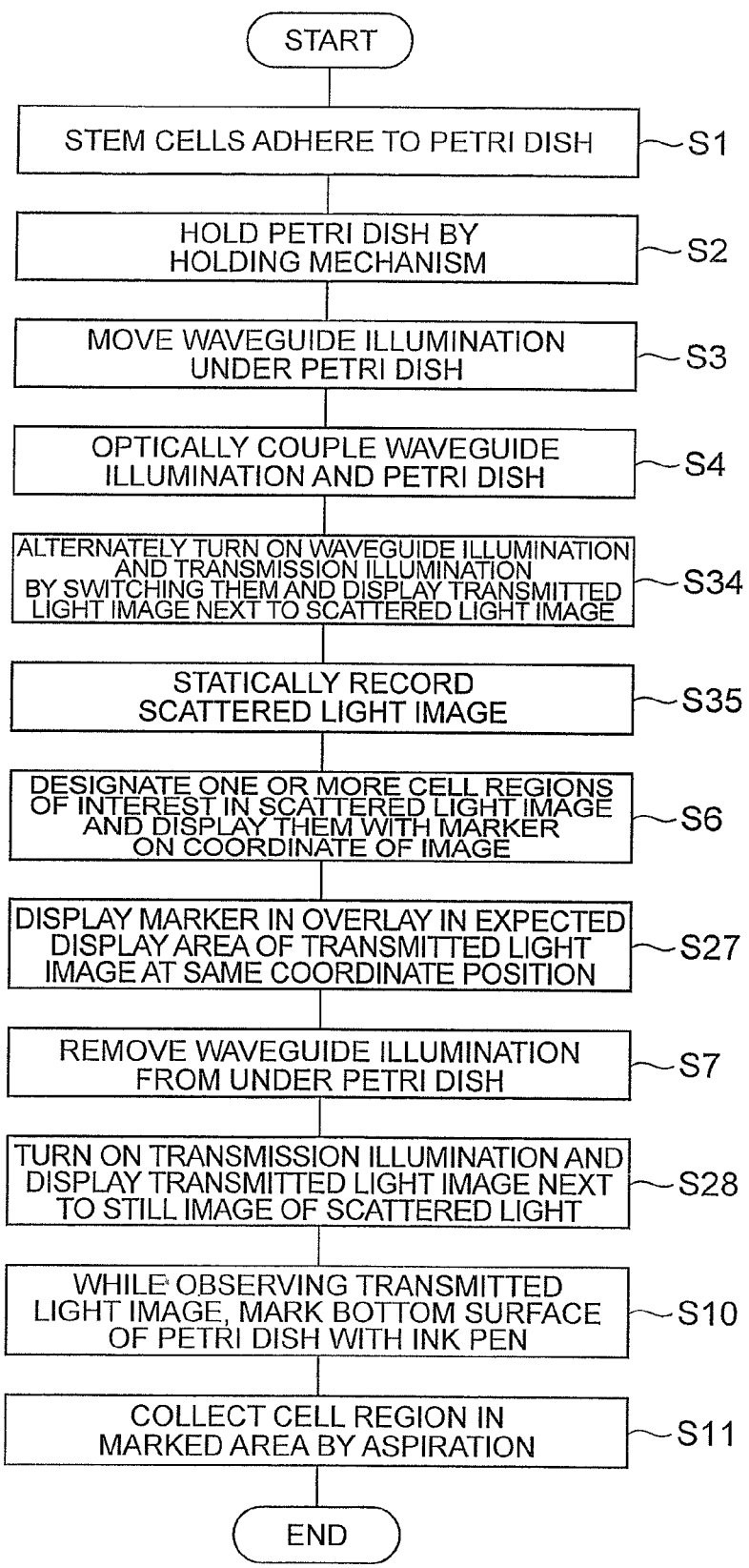
FIG. 16 is a flowchart illustrating a modification example of the observation method illustrated in FIG. 15.

According to the aforementioned embodiment, the transmitted light image is displayed after the scattered light image is displayed; however, for example, as illustrated in FIG. 16, it is also possible to alternately turn on the light irradiation devices 20A and 20B by switching them, select a scattered light image and a transmitted light image, display them on the display device 50, and then record a still image of the scattered light image (steps S34 and S35). As shown above, it is made even easier for the observer to recognize the position of a cell colony in the state tending toward differentiation in a transmitted light image by alternately displaying both images when the scattered light image is displayed. The modification example of the observation method illustrated in FIG. 16 is the same as the observation method illustrated in FIG. 14, except for the steps S34 and S35.

The preferred embodiments of the present invention have been described in detail heretofore; however, the present invention is not limited to the aforementioned embodiments, and various modifications are possible. For example, it is also possible to control display so that the vertical and horizontal display directions of the image displayed on the display device 50 match the vertical and horizontal directions of operation to make the operation of marking the bottom surface of the petri dish 11 easy. Also, while the marking device 60 has an ink pen, other marking devices may also be used. Further, when the position of a cell colony in the state tending toward differentiation is marked on the scattered light image, it is also possible to correlate the position thus marked to the position of cells in the petri dish 11 by the control device 40 and remove a cell colony in the state tending toward differentiation by laser and the like according to the correlated position information, instead of marking the petri dish 11 by the marking device 60. Also, although observation was performed by placing the cells to be observed on the bottom surface of the container in the aforementioned embodiments, no limitation is imposed, and it may also be possible to observe suspension cells suspended in culture medium in a container by the observation method using the aforementioned observation device.

INDUSTRIAL APPLICABILITY

The present invention is applicable to an observation method or observation device for distinguishing between the undifferentiated state and the state tending toward differentiation of stem cells.

REFERENCE SIGNS LIST

1 . . . Observation device, 10 . . . Sample holding unit, 11 . . . Petri dish, 20A and 20B . . . Light irradiation device, 21 . . . Waveguide, 22 . . . Light source device, 23 . . . Moving device, 30 . . . Image acquisition device, 40 . . . Control device, 50 . . . Display device, 60 . . . Marking device, C . . . Stem cell, L2 . . . Scattered light, L4 . . . Transmitted light

The invention claimed is:

1. A method for observing stem cells, comprising:
    irradiating stem cells placed on a transparent member with oblique illumination light;
    capturing a scattered light image of the stem cells by a camera having a two dimensional pixel structure, in which a plurality of pixels are two-dimensionally arranged; and
    identifying a stem cell that is in the state tending toward differentiation in the sterm cells based on the scattered light image,
    wherein the irradiating irradiates the stem cells with the oblique illumination light via the transparent member.

2. The method according to claim 1, wherein the identifying identifies a darker portion in the scattered light image of the stem cell that is in the state tending toward differentiation.

3. The method according to claim 1, wherein the capturing images light that is scattered by the stem cells and passed through the transparent member.

4. The method according to claim 1, further comprising, irradiating the stem cells placed on the transparent member with transmitted illumination light; and
    capturing a transmitted light image of the stem cells by the camera.

5. The method according to claim 1, further comprising, removing the identified stem cell from the stem cells.

6. The method according to claim 1, wherein the stem cells are iPS cells.

7. An apparatus for observing stem cells, comprising:
    a light source configured to output light;
    an illumination optics configured to input the output light and irradiate stem cells placed on a transparent member with oblique illumination light;
    a camera having a two dimensional pixel structure, in which a plurality of pixels are two-dimensionally arranged and configured to capture a scattered light image of the stem cells; and
    a display configured to display the scattered light image, thereby identifying a stem cell that is in the state tending toward differentiation in the stem cells,
    wherein the illumination optics irradiates the stem cells with the oblique illumination light via the transparent member.

8. The apparatus according to claim 7, wherein the camera images light that is scattered by the stem cells and passed through the transparent member.

9. The apparatus according to claim 7, wherein the illumination optics comprises a light guide having a surface on which the transparent member can be mounted and another surface inputting the output light.

10. The apparatus according to claim 9, wherein the camera images light that is scattered by the stem cells and passed through the transparent member and the light guide.

11. The apparatus according to claim 7, wherein the stem cells are iPS cells.

12. An apparatus for observing stem cells, comprising:
    a light source configured to output light;
    an illumination optics configured to input the output light and irradiate stem cells placed on a transparent member with oblique illumination light;
    a camera having a two dimensional pixel structure, in which a plurality of pixels are two-dimensionally arranged and configured to capture a scattered light image of the stem cells; and
    a display configured to display the scattered light image, thereby identifying a stem cell that is in the state tending toward differentiation in the stem cells,
    wherein the illumination optics comprises a light guide having a surface on which the transparent member can be mounted and another surface inputting the output light.

13. The apparatus according to claim 12, wherein the camera images light that is scattered by the stem cells and passed through the transparent member.

14. The apparatus according to claim 12, wherein the stem cells are iPS cells.

* * * * *